US008337700B1

(12) United States Patent
Zuk, Jr.

(10) Patent No.: US 8,337,700 B1
(45) Date of Patent: Dec. 25, 2012

(54) HIGH CAPACITY BIOLOGICAL FLUID FILTRATION APPARATUS

(75) Inventor: Peter Zuk, Jr., Harvard, MA (US)

(73) Assignee: Hemerus Medical, LLC, St. Paul, MN (US)

( * ) Notice: Subject to any disclaimer, the term of this patent is extended or adjusted under 35 U.S.C. 154(b) by 184 days.

(21) Appl. No.: 11/360,129

(22) Filed: Feb. 23, 2006

Related U.S. Application Data (60) Provisional application No. 60/656,072, filed on Feb. 24, 2005.

(51) Int. Cl.
*B01D 11/00* (2006.01)
*B01D 37/00* (2006.01)
*A61B 19/00* (2006.01)

(52) U.S. Cl. ............... 210/645; 210/321.6; 210/335; 210/436; 210/472; 210/767; 604/406

(58) Field of Classification Search ............ 210/335, 210/321, 321.6, 493.4, 645, 767; 604/406
See application file for complete search history.

(56) References Cited

U.S. PATENT DOCUMENTS

| | | | | |
|---|---|---|---|---|
| 3,593,854 A | * | 7/1971 | Swank | 210/326 |
| 5,591,337 A | * | 1/1997 | Lynn et al. | 210/489 |
| 6,231,770 B1 | * | 5/2001 | Bormann et al. | 210/767 |
| 7,332,096 B2 | * | 2/2008 | Blickhan | 210/767 |
| 2003/0236481 A1 | * | 12/2003 | Burbank | 604/5.01 |
| 2004/0011723 A1 | * | 1/2004 | Bradford et al. | 210/321.74 |
| 2005/0133439 A1 | * | 6/2005 | Blickhan | 210/323.1 |

* cited by examiner

*Primary Examiner* — Krishnan S Menon
*Assistant Examiner* — Dirk Bass
(74) *Attorney, Agent, or Firm* — Marshall & Melhorn, LLC (57) ABSTRACT

A biological fluid filtration device, system, and method, for filtering a biological fluid, the device comprising a housing having an inlet, a first outlet and a second outlet, with a first fluid flow path defined between the inlet and the first outlet, with a second fluid flow path defined between the inlet and the second outlet, with a first biological fluid filtration media interposed between the inlet and the first outlet and across the first fluid flow path, with a second biological fluid filtration media interposed between the inlet and the second outlet and across the second fluid flow path, the housing essentially lacking a solid partition wall between the first biological fluid filtration media and the second biological fluid filtration media, a first flow restriction may be added downstream of the first biological fluid filtration media, and a second flow restriction may be added downstream of the second biological fluid filtration media, in another embodiment, the device comprises a housing having an inlet an outlet with a flow path defined between the inlet and the outlet, with a biological fluid filtration media interposed between the inlet and the outlet and across the fluid flow path, the device further including a flow restriction downstream of the biological fluid filtration media.

20 Claims, 6 Drawing Sheets

HIGH CAPACITY BIOLOGICAL FLUID FILTRATION APPARATUS

Pursuant to 35 U.S.C. §119(e)(i), applicant claims priority of Provisional Application Ser. No. 60/656,072 filed: Feb. 24, 2005.

BACKGROUND OF THE INVENTION

This invention relates to the filtration field, and more particularly, to an improved low hold up biological fluid filtration system, including a low hold up double sided biological fluid filter device lacking a partition wall capable of filtering biological fluids, including the removal of components or chemicals from blood or blood products, and including the removal of leukocytes from packed red cells, and prions from blood or blood products.

Double sided biological fluid filtration devices that include a single inlet and a single outlet with a partition wall are disclosed in patent serial no. U.S. Pat. No. 6,660,171 B2, entitled HIGH CAPACITY GRAVITY FEED FILTER FOR FILTERING BLOOD AND BLOOD PRODUCTS, filed on Mar. 27, 2001 which is hereby incorporated by reference and made a part of the disclosure herein. Double sided biological fluid filtration devices that contain a partition wall are also disclosed in patent application Ser. No. 10/934,881, entitled A BIOLOGICAL FLUID FILTRATION APPARATUS, filed on Sep. 3, 2004 which is hereby incorporated by reference and made a part of the disclosure herein. Double sided biological fluid filtration devices that contain a partition wall are also disclosed in PCT application no. PCT/US2004/029026, entitled A BIOLOGICAL FLUID FILTRATION APPARATUS, filed on Sep. 7, 2004 which is hereby incorporated by reference and made a part of the disclosure herein. Application Ser. No. 10/934,881 and application no. PCT/US2004/029026 disclose a double sided biological fluid filtration device that includes two independent fluid flow paths separated by a partition wall with each fluid flow path containing a separate inlet and outlet, thereby allowing two units of biological fluid including blood or blood product to be independently filtered.

U.S. Pat. No. 6,231,770 B1 describes a double sided biological fluid filtration device that lacks a partition wall that includes a single inlet and a single outlet with two fluid flow paths between the inlet and outlet. The disadvantage of this type of device is that if two units of blood or blood product are filtered through this device and collected into two separate receiving blood bags, the first unit will be filtered by the device with the filter elements of the device in a relatively non-fouled condition, and the second unit will be filtered by the device with the filter elements in a relatively fouled condition. Therefore the flow rate through the device for the first unit will be faster than the flow rate for the second unit. Hence the filtration efficiency may be different between the first and second units, and when the device is used for leukocyte reduction the leukocyte reduction rate may be different for the first and second units.

It is therefore an object of the present invention to provide a biological fluid filtration system including a biological fluid filtration device that lacks a partition wall, and that includes a single inlet and a double outlet, that will filter two units of biological fluid including blood or blood product, with both units being filtered simultaneously at approximately the same flow rate, and that will run automatically, and minimize hold up volume. It is also an object of the present invention to provide a single vent filtration device that can vent the two fluid flow paths of a biological fluid filtration device that includes two independent fluid flow paths.

DEFINITIONS

A Double Sided Biological Fluid Filtration Device (hereinafter referred to as BFFD) as used herein means a filtration device comprising a housing containing an inlet and two outlets, with a first fluid flow path defined between the inlet and the first outlet, with a second fluid flow path defined between the inlet and the second outlet, with a first biological fluid filtration media interposed between the inlet and the first outlet and across the first fluid flow path, with the first biological fluid filtration media sealed to the housing to prevent the flow of biological fluid between the housing and the first biological fluid filtration media, with a second biological fluid filtration media interposed between the inlet and the second outlet and across the second fluid flow path, with the second biological fluid filtration media sealed to the housing to prevent the flow of biological fluid between the housing and the second biological fluid filtration media. The biological fluid filtration device being capable of filtering biological fluids, including blood or blood products to remove leukocytes, prions, other blood components, cells, and chemical agents which may be used to treat the biological fluid, from the biological fluid.

Biological Fluid Filtration Media (hereinafter referred to as BFFM) as used herein means a porous filtration media capable of filtering biological fluids, including blood or blood products to remove leukocytes, prions, other blood components, cells, and chemical agents which may be used to treat the biological fluid, from the biological fluid. The biological fluid filtration media (BFFM) comprises at least one filter element, with each filter element containing one or more layers of porous filter material of the same type. The biological fluid filtration media may contain more than one filter element, with each filter element containing a different type of filter material. Any of the various types of biological fluid filtration media that contain one or more filter elements of the same or different types as disclosed in patent application Ser. No. 10/934,881 or in application no. PCT/US2004/029026 may be considered as biological fluid filtration media in this application.

Vent Filtration Media as used herein means the filtration media used in a vent filter device. The media may be microporous filter material made from a material such as TEFLON (polytetrafluoroethylene) or PVDF, preferably with a pore size of 0.2μ or smaller, or the media may be a depth media, such as cotton, spun bound polyester, or a molded depth media such as POREX.

Housing as used herein means the enclosure into which the filtration media is sealed. The housing of a BFFD contains an inlet and two outlets, with a first fluid flow path defined between the inlet and the first outlet, with a first BFFM interposed between the inlet and the first outlet and across the first fluid flow path, and sealed to the housing to prevent the flow of biological fluid between the housing and the first BFFM; with a second fluid flow path defined between the inlet and the second outlet, with a second BFFM interposed between the inlet and the second outlet and across the second fluid flow path, and sealed to the housing to prevent the flow of biological fluid between the housing and the second BFFM. The housing does not contain a partition wall. The housing may be made from a rigid material such as stainless steel or aluminum, or from any rigid molded plastic material such as Acrylic, Polycarbonate, Polypropylene, Polyethylene. The housing of a vent filtration device contains a vent port in fluid flow communication with atmosphere, and a system port in fluid flow communication with the biological fluid filtration system, with a fluid flow path defined between the vent port and the system port, with a vent filtration media interposed between the vent port and the system port and across the fluid flow path, and sealed to the housing to prevent the flow of biological fluid or gas between the vent filtration media and the housing.

Biological Fluid as used herein means any type of biological liquid, including blood or blood product, and including leukocyte containing suspensions or a prion containing suspensions.

Leukocyte Containing Suspension as used herein means a liquid in which leukocytes are suspended. Examples of leukocyte-containing suspensions include whole blood; red cell products, such as concentrated red cells, washed red cells, leukocyte-removed cells, thawed red cell concentrate and thawed red cell suspension; plasma products, such as platelet-poor plasma, platelet-enriched plasma, fresh lyophilized plasma, fresh liquid plasma and cryoprecipitate; and other leukocyte-containing blood products, such as concentrated platelet cells, buffy coat and buffy coat-removed blood. The leukocyte-containing suspension to be filtered by the devices and systems described in the present invention is not limited to the above examples.

Prion Containing Suspension as used herein means a liquid in which prions are suspended.

Diaphragm Draining Device (hereinafter referred to as DDD) as used herein means a device having a housing with an inlet in fluid flow communication with atmosphere, with an outlet in fluid flow communication with a second device to be drained, and with a diaphragm interposed between the inlet and the outlet, with the housing containing a volume of gas between the diaphragm and the outlet in its normal state.

SUMMARY OF THE INVENTION

The foregoing problems of the prior art are solved, and the objects of the present invention are achieved, by use of a biological fluid filtration device (BFFD) and system constructed in accordance with the principles of the present invention. The biological fluid filtration system of the present invention is capable of filtering biological fluids, including blood or blood products to remove leukocytes, prions, other blood components, cells, and chemical agents which may be used to treat the biological fluid, from the biological fluid.

The biological fluid filtration system includes a feed container, normally a collapsible blood bag and a receiving container, normally a collapsible blood bag with a BFFD interposed between the two blood bags. The BFFD includes a housing lacking a partition wall having an inlet and two outlets, with a first fluid flow path defined between the inlet and the first outlet, with a first biological fluid filtration media (BFFM) is interposed between the inlet and the first outlet, and across the first fluid flow path; and with a second fluid flow path defined between the inlet and the second outlet, with a second biological fluid filtration media (BFFM) interposed between the inlet and the second outlet, and across the second fluid flow path. The BFFM's may contain one filter element or multiple filter elements of different types. The housing also includes a chamber located between the inlet and the upstream surface of the two BFFM's. A first flow restriction may be located downstream of the first BFFM, and a second flow restriction may be located downstream of the second BFFM. The biological fluid filtration system also includes a means to automatically drain the upstream chamber of the BFFD when the filtration cycle is complete. The draining means may include a diaphragm draining device (D D D) that includes a built in flow restriction. Any of the various types of in line automatic draining means that are disclosed in patent application Ser. No. 10/934,881 or in application no. PCT/US2004/029026 may be used as automatic draining means in this application.

In any of the embodiments the BFFM may include a first filter element composed of one or more layers of porous filter material of a first pore size, followed by a second filter element composed of one or more layers of porous filter material of a second pore size smaller than that of the first pore size, followed by a third filter element composed of one or more layers of porous filter material of a third pore size larger than that of the second pore size, followed by a fourth filter element composed of one or more layers of porous filter material of a fourth pore size smaller than the pore size of the second filter element. The first filter element may include means to remove gels from blood or blood product, the second filter element may include means to remove microaggregates from blood or blood products, the fourth filter element may include means to remove leukocytes from blood or blood products, while the third filter element acts as a flow distribution layer. However, the BFFM is not restricted to the type just described, any suitable type of BFFM for a particular application may be used.

BRIEF DESCRIPTION OF THE DRAWINGS

The invention may be best understood by reference to the detailed description of the preferred embodiments herein when read in conjunction with the drawings in which.

DETAILED DESCRIPTION OF THE FIRST EMBODIMENT

One embodiment of the biological fluid filtration system constructed in accordance with the principles of the present invention, is shown in FIG. 1 through FIG. 5. Biological fluid filtration system 1000 shown in FIG. 1 contains feed blood 98, first receiving blood bag 99 and second receiving blood bag 99a. Interposed between feed blood bag 98 and the two receiving blood bags is a biological fluid filtration device (BFFD) 100. Diaphragm draining device (DDD 50) is interposed between feed blood bag 98 and BFFD 100. First length of tubing 81 connects the outlet of feed blood bag 98 to the inlet tube socket 51 of DDD 50. Second length of tubing 81a connects outlet tube socket tube socket 52 of DDD 50 to the inlet tube socket 6 of BFFD 100. A third length of tubing 82 connects first outlet tube socket 28 of BFFD 100 to the inlet of first receiving blood bag 99. A fourth length of tubing 82a connects second outlet tube socket 28a of BFFD 100 to the inlet of second receiving blood bag 99a. Tubing 81 may contain tube clamp 95, tubing 82 may contain tube clamp 96, tubing 82a may contain tube clamp 96a.

Referring to FIG. 2 through FIG. 5, BFFD 100 contains a rigid housing that includes housing inlet half 1, first housing outlet half 20, and second housing outlet half 20a. Housing seal surface 19 of housing inlet half 1 is bonded to housing seal surface 29 of first housing outlet half 20. Housing seal surface 19a of housing inlet half 1 is bonded to housing seal surface 29a of second housing outlet half 20a. The bonds are preferably ultrasonic welds but could be a heat bonds, glue bonds, solvent bonds, or any other type of leak tight bonds.

Figure 2:
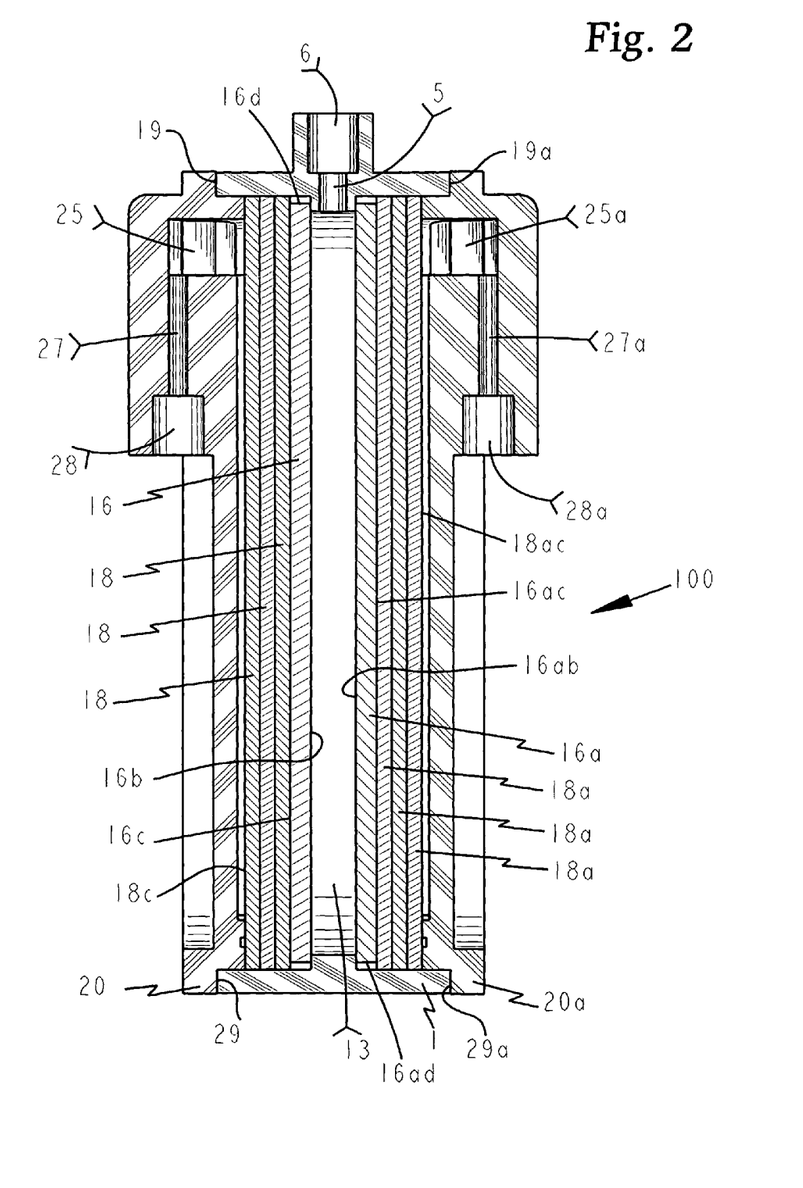
FIG. 2 is a cross-sectional view of the first embodiment of a BFFD constructed in accordance with the principles of the present invention, usable for the filtration of biological fluids.
Figures 3, 4:
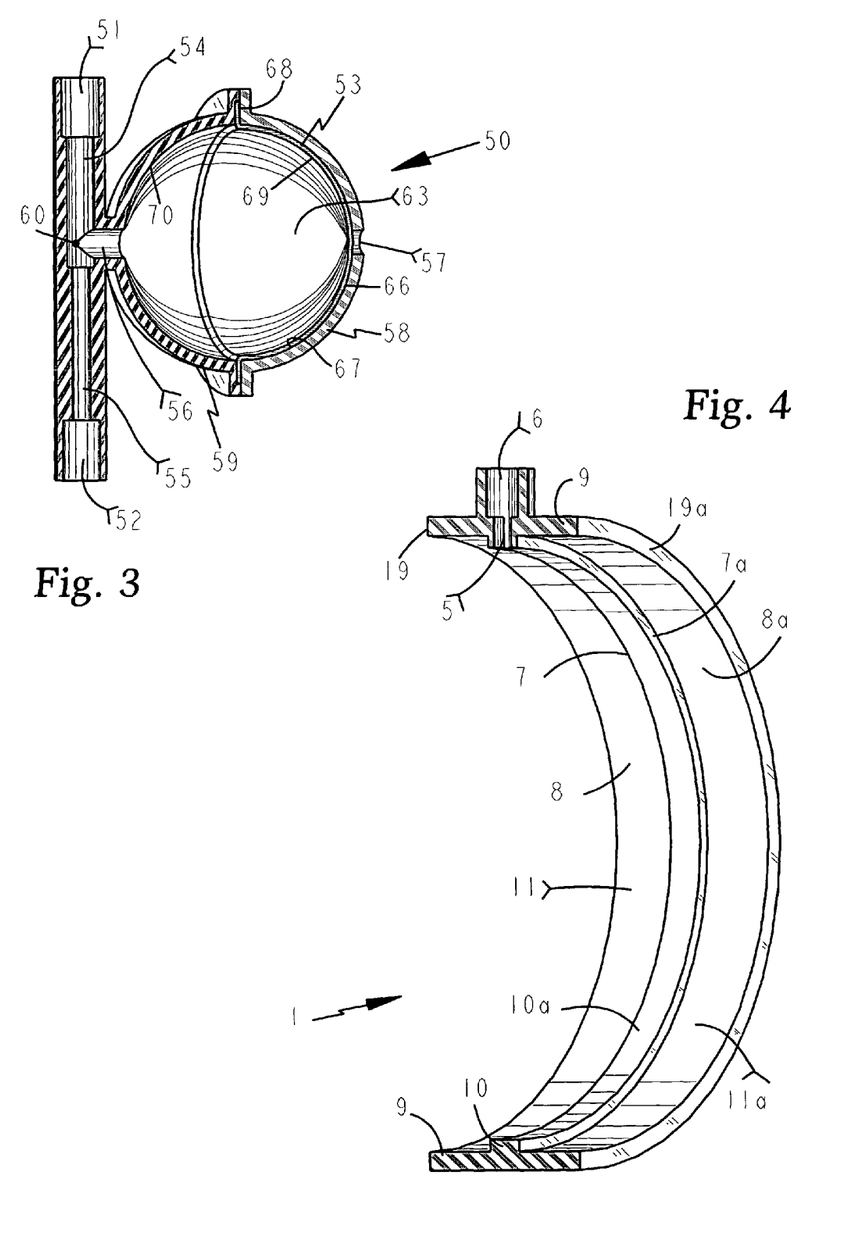
FIG. 3 is an isometric view with portions thereof removed of the DDD shown in FIG. 1.
FIG. 4 is a isometric view with portions thereof removed of the housing inlet half of the BFFD shown in FIG. 2.
Figure 5:
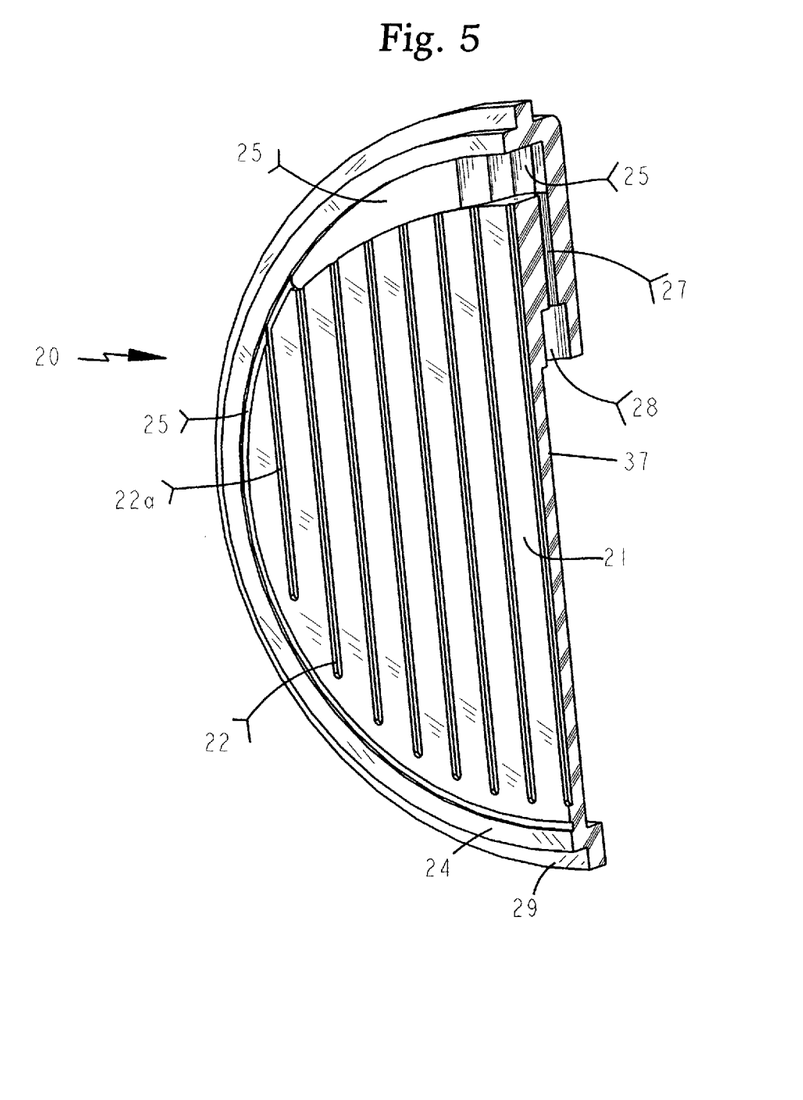
FIG. 5 is an isometric view with portions thereof removed of the first housing outlet half of the BFFD shown in FIG. 2, the second housing outlet half is identical to the first housing outlet half.

Referring to FIG. 2, FIG. 4, and FIG. 5 housing inlet half 1 contains first filter well 11 bounded by inner side wall 8 and by a plane that goes through filter seal surface 7. Housing inlet half 1 also contains second filter well 11a bounded by inner side wall 8a and by a plane that goes through filter seal surface 7a. Upstream chamber 13 is bounded by inner surface 10a of inner wall 10 of housing inlet half 1, and by upstream surface 16b of filter element 16, and by upstream surface 16ab of filter element 16a. Hence upstream chamber contains a space between the upstream surface of the first BFFM and the upstream surface of the second BFFM, with the upstream surface of the first BFFM opposing the upstream surface of the second BFFM. The first and second BFFM's are further defined below. Inlet 5 is in fluid flow communication with upstream chamber 13. The outlet end of tubing 81a is inserted into and bonded to inlet tube socket 6. Inlet 5 is shown located at the top of upstream chamber 13 and on the vertical center line of housing inlet half 1, it could however, be located anywhere between the top and the bottom of upstream chamber 13, and could also be located to the right or to the left of the vertical center line.

Referring to FIG. 2 and FIG. 5, BFFD 100 contains first housing outlet half 20 and second housing outlet half 20a. Housing outlet half 20a is identical to housing outlet half 20. Housing outlet half 20 contains circular outlet channel 25 and outlet 27. Outlet 27 may contain a flow restriction as shown in FIG. 2 and FIG. 5. Circular outlet channel 25 is in direct fluid flow communication with outlet 27, and the portion of circular outlet channel 25 that adjoins outlet 27 has a cross-sectional flow area that is greater than the cross-sectional flow area of outlet 27. Housing outlet half 20 also contains a plurality of open top closed bottom vertical channels 22 and 22a. One end of each of the vertical channels 22 and 22a is in fluid flow communication with circular outlet channel 25. The upper part of circular outlet channel 25 increases in width to accommodate the flow of biological fluid from vertical channels 22 and 22a. The width of the remainder of circular outlet channel 25 (i.e. the lower part of circular outlet channel 25) is preferably equal to the width of the vertical channels. The two outermost vertical channels designated as vertical channels 22a adjoin circular outlet channel 25 where the width of circular outlet channel 25 is equal to the width of the vertical channels. The outlet channel and the vertical channels combined, create a filter under drain structure that is cut into wall 37 of housing outlet half 20 so that the inner surface of all of the channels lies below inner wall 21 of housing outlet half 20 as shown in FIG. 5. The cross sectional area the outlet channel and of the vertical channels is defined by the inner surface of each channel and by the downstream surface of the BFFM. As shown in FIG. 5, the distance between vertical channels 22 and 22a is much greater than the width of vertical channels 22 and 22a, and the distance between vertical channels 22 and 22a is also much greater than the depth of vertical channels 22 and 22a. For example, the center line distance between the vertical channels may be equal to 0.150 in., with the width of the vertical channels equal to 0.032 in., and with the depth of the vertical channels equal to 0.025 in. Housing outlet half 20 also contains filter seal surface 24. Because housing outlet half 20 does not contain an open chamber or plenum downstream of the BFFM, hold up volume of biological fluid will be minimized. Housing outlet half 20 of this application is identical to housing outlet half 220 that is disclosed in patent application Ser. No. 10/934,881 and in application no. PCT/US2004/029026, with the exception that housing outlet half 220 does not contain a flow restriction in the outlet.

Referring to FIG. 2, a first biological fluid filtration media (BFFM) that contains at least one filter element is interposed between inlet 5 and first outlet 27, and is sealed to the housing to prevent the flow of unfiltered biological fluid from flowing between the housing and the first BFFM to prevent bypass of unfiltered biological fluid around the first BFFM. A second biological fluid filtration media (BFFM) that contains at least one filter element is interposed between inlet 5 and second outlet 27a, and is sealed to the housing to prevent the flow of unfiltered biological fluid from flowing between the housing and the second BFFM to prevent bypass of unfiltered biological fluid around the second BFFM. The first BFFM shown in FIG. 2 contains filter elements 16 and 18. The filter elements may all be of the same type or may be different types filter elements. For example filter element 16 may be a microaggregate filter element and filter elements 18 may be leukocyte removing filter elements. Each filter element contains an upstream surface designated as upstream surface 16b for filter element 16, a downstream surface designated as downstream surface 16c for filter element 16, and a perimeter surface designated as perimeter surface 16d for filter element 16. The downstream surface of the BFFM shown as downstream surface 18c of filter element 18 is in contact with inner wall 21 of housing outlet half 20. Because the downstream surface of the BFFM contacts inner wall 21 of housing outlet half 20, BFFD 100 does not contain an open chamber or plenum downstream of the BFFM. The air or liquid that is forced through the BFFM must pass through the vertical channels and the circular outlet channel before flowing into outlet 27 of BFFD 100. The at least one filter element may be sealed to the housing with an interference fit between the perimeter surface of the at least one filter element and inner side wall 8 of housing inlet half 1 as shown for filter elements 18, or the at least one filter element may be sealed to the housing with a compression seal by compressing the outer periphery of the at least one filter element with filter seal surface 7 of housing inlet half 1 as shown for filter element 16, or the at least one filter element may be sealed to the housing a heat seal, an ultrasonic weld, a glue seal, a solvent seal, a radio frequency weld, or any other type of leak tight seal. A combination of sealing methods may also be used to seal the at least one filter element to the housing. The second BFFM is preferably the same as the first BFFM and is preferably sealed to the housing the same way that the first BFFM is sealed to the housing. Any of the filter element combinations that are disclosed in patent application Ser. No. 10/934,881 and in application no. PCT/US2004/029026, can also be used in the present invention. For example a gel filter element followed by a microaggregate filter element, followed by a flow distribution filter element, followed by a leukocyte removing filter element could be used in the present invention.

Referring to FIG. 2 and FIG. 5, a first fluid flow path is defined between inlet 5 of BFFD 100 and first outlet 27 of BFFD 100 with the at least one filter element of the first BFFM interposed between inlet 5 and first outlet 27, and across the fluid flow path. The first fluid flow path flows from inlet 5, into upstream chamber 13, through the at least one filter element of the first BFFM, into vertical channels 22 and 22a, into circular outlet channel 25, and then into outlet 27 which may contain a flow restriction, all of first housing outlet half 20. A second fluid flow path is defined between inlet 5 of BFFD 100 and second outlet 27a of BFFD 100 with the at least one filter element of the second BFFM interposed between inlet 5 and second outlet 27a, and across the second flow path. The second fluid flow path flows from inlet 5, into upstream chamber 13, through the at least one filter element of the second BFFM, into vertical channels 22 and 22a, into circular outlet channel 25, and then into outlet 27a which may contain a flow restriction, all of second housing outlet half 20a.

Figure 1:
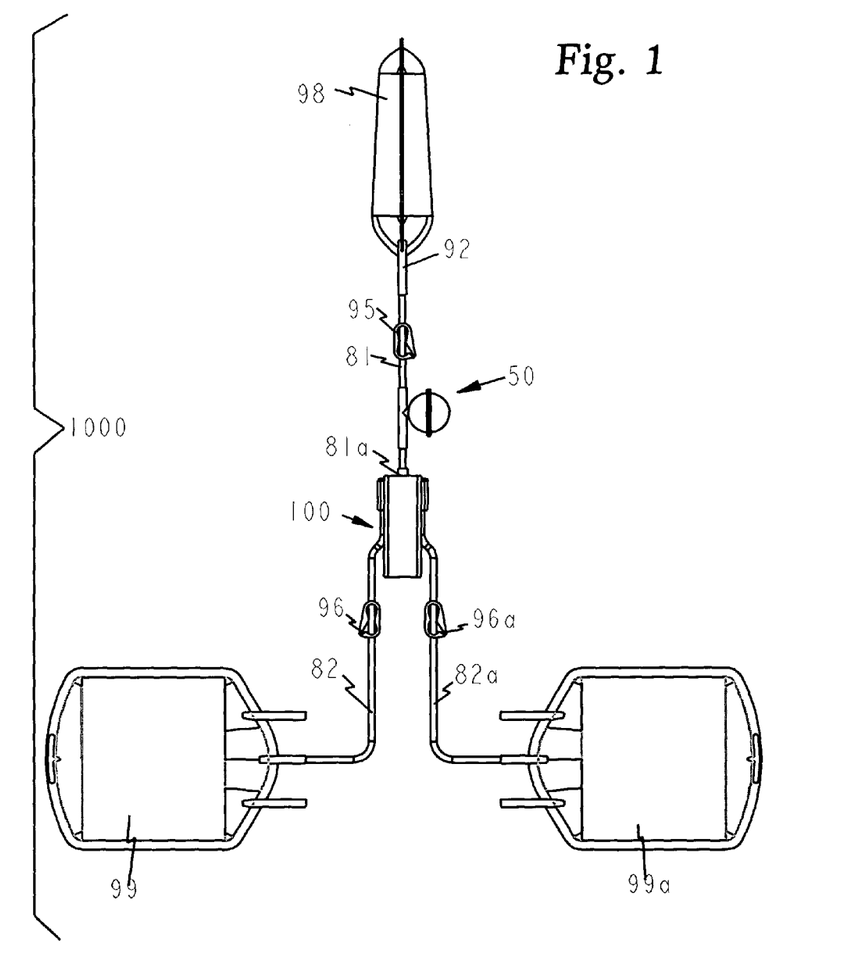
FIG. 1 is an isometric view of a first embodiment of a biological fluid filtration system constructed in accordance with the principles of the present invention, usable for the filtration of biological fluids, containing a feed blood bag, a first receiving blood bag, a second receiving blood bag, with the first embodiment of a BFFD interposed between the feed blood bag and the receiving blood bag, and with a diaphragm draining device (DDD) that includes a built in flow restriction interposed between the feed blood bag and the BFFD.

FIG. 1 and FIG. 3 show diaphragm draining device 50 (hereinafter referred to as DDD 50). DDD 50 contains rigid housing inlet half 58, rigid housing outlet half 59 and flexible diaphragm 53. Housing outlet half 59 contains inlet tube socket 51, outlet tube socket 52, first channel 54, second channel 55, third channel 56, and common node 60. Common node 60 (shown as a dot) places each one of the three channels in fluid flow communication with the other two channels. Second channel 55 contains a flow restriction shown as a channel that is longer and smaller in diameter than the first and third channels. The first channel may be referred to as inlet 54, the second channel may be referred to as outlet 55, and the third channel may be referred to as side port 56. Housing outlet half 59 combines three tube connector 1650 and housing outlet half 1820 that are disclosed in patent application Ser. No. 10/934,881 and in application no. PCT/US2004/029026 into a single component. The shape of the three tube connector made up of first channel 54, second channel 55, and third channel 56, is shown as a tee, but is not restricted to this shape, it could be in the form of a Y, for example. FIG. 3 shows DDD 50 in its normal state with housing inlet half 58 sealed to housing outlet half 59. The seal is preferably an ultrasonic seal, but could be a heat seal, a solvent seal, a glue seal, or a compression seal between housing inlet half 58 and housing outlet half 59, or any other type of leak tight seal. Flexible diaphragm 53 may be molded from a flexible rubber material such as silicone rubber, or it may be molded or thermo formed from a material such as PVC, polyethylene, or polypropylene, but is not limited to these materials. Flexible diaphragm 53 is preferably shaped so that in its normal state outer surface 66 conforms to inner surface 67 of housing inlet half 58. Flexible diaphragm 53 contains flange 68 which may be bonded to housing inlet half 58 or to housing outlet half 59. The bond may be a heat bond, an ultrasonic bond, a glue bond, a solvent bond, or any other type of leak tight bond. Alternately, flange 68 may be compression sealed between housing inlet half 58 and housing outlet half 59. FIG. 3 shows DDD 50 in its normal state with outer surface 66 of diaphragm 53 in contact with inner surface 67 of housing inlet half 58. In its normal state, DDD 50 contains chamber 63 that is in fluid flow communication with third channel 56. In the normal state chamber 63 is filled with a gas (normally sterile air) at atmospheric pressure. When diaphragm 53 is completely collapsed inner surface 69 of diaphragm 53 will contact inner surface 70 of housing outlet half 59.

Referring to FIG. 1 through FIG. 3, a third fluid flow path is defined between feed blood bag 98 and common node 60 of housing outlet half 59 of DDD 50, with the flow in the third fluid flow path flowing from feed blood bag 98 through tubing 81, into inlet 54 of DDD 50, to common node 60. A fourth fluid flow path is defined between common node 60 of DDD 50 and inlet 5 of BFFD 100, with the flow in the fourth fluid flow path flowing from common node 60, through outlet 55 of DDD 50 (including the flow restriction), through tubing 81a, to inlet 5 of BFFD 100. A fifth fluid flow path is defined between the common node and chamber 63 of DDD 50, with the flow of the fifth fluid flow path flowing from chamber 63, through third channel 56, to the common node 60.

Referring to FIG. 1 through FIG. 5, biological fluid filtration system 1000 functions as follows. The user will purchase the system with all components as shown in FIG. 1, less feed blood bag 98. The user will connect tubing 81 to outlet 92 of feed blood bag 98 in a manner known in the art. Feed blood bag 98 may be hung from a hook on a blood bag pole, and first receiving blood bag 99 and second receiving blood bag 99a may be placed on a table top or the like, so that the various components of the system will be positioned as shown in FIG. 1. Alternately feed blood bag 98 may be part of a set that includes all of the components shown in FIG. 1, in which case the blood or blood product that is collected from a donor will be collected in feed blood bag 98. Tube clamp 95 should be closed before connecting tubing 81 to feed blood bag 98. Before opening tube clamp 95 to start the flow of biological fluid (i.e. liquid) through the system, tube clamps 96 and 96a should be open.

When tube clamp 95 is opened biological fluid (i.e. liquid) will flow from feed blood bag 98, through tubing 81, into inlet 54 of DDD 50, through outlet 55 of DDD 50, through tubing 81a, into inlet 5 of BFFD 100, into upstream chamber 13 of BFFD 100. Because outlet 55 of DDD 50 contains a flow restriction, the flow downstream of the inlet and downstream of the side port of the DDD will be automatically restricted, and a positive pressure will be created at common node 60 of DDD 50. Also because flexible diaphragm 53 is sealed to DDD 50 with a liquid/air tight seal, air can not escape through inlet 57 of DDD 50. Therefore the air in chamber 63 of DDD 50 will be pressurized so that only a very small quantity of biological fluid if any will enter side port 56 of DDD 50.

Once tube clamp 95 is opened, one of four conditions can occur. The first condition is: If the volume of upstream chamber 13 is small enough, and if the initial combined flow rate of the first and second BFFM's does not exceed the flow rate of the biological fluid entering inlet 5, upstream chamber 13 of BFFD 100 will rapidly fill with biological fluid from the bottom up. As upstream chamber 13 fills from the bottom up, the initial air in upstream chamber 13 will be displaced by the biological fluid filling upstream chamber 13. A portion of the displaced air will be forced through the first BFFM, into vertical channels 22 and 22a, into circular outlet channel 25, and then into outlet first 27, all of first housing outlet half 20. The remainder of the displaced air will be forced through the second BFFM, into vertical channels 22 and 22a, into circular outlet channel 25, and then into second outlet 27a, all of second housing outlet half 20a. The biological fluid in upstream chamber 13 will be pressurized, with the pressure at the bottom of upstream chamber 13 being proportional to the distance from the top of the biological fluid in feed blood bag 98 to the bottom of upstream chamber 13, and with the pressure at the top of upstream chamber 13 being proportional to the distance from the top of the biological fluid in feed blood bag 98 to the top of upstream chamber 13. Hence the pressure at the top of upstream chamber 13 will be less than the pressure at the bottom of upstream chamber 13. The positive pressure in upstream chamber 13 will cause the biological fluid to flow through the first and second BFFM's over the entire surface area of the first and second BFFM's and to displace the air within the pores of the first and second BFFM's with biological fluid, thereby wetting the first and second BFFM's from the upstream side of the first and second BFFM's to the downstream side of the first and second BFFM's. As the BFFM's wet the air that was initially in the pores of BFFM's will be displaced by biological fluid and flow into the vertical channels 22 and 22a, and into circular outlet channel 25, of the respective housing outlet half's, and then into outlet 27 of housing outlet half 20 and outlet 27a of housing outlet half 20a, into tubing 82, and then into first receiving blood bag 99, and into tubing 82a, and then into second receiving blood bag 99a. Because the pressure at the bottom of upstream chamber 13 is greater than the pressure at the top of upstream chamber 13, the initial flow rate of biological fluid through the BFFM's will be greater at the bottom of the BFFM's than at the top of the BFFM's. Therefore, the BFFM's will first become completely wetted from the upstream surface of the BFFM's to downstream surface of the BFFM's at the bottom of the BFFM's. If the width of vertical channels 22 and 22a of the respective housing outlet half's is sufficiently small, and the depth of vertical channels 22 and 22a is sufficiently shallow, so that the cross-sectional flow area of vertical channels 22 and 22a is sufficiently small, and if the distance between vertical channels 22 is sufficiently large, the path of least resistance for continued biological fluid flow through the BFFM's will be through the capillaries of the BFFM's in both the horizontal and vertical directions and not through the vertical channels; because if the cross-sectional flow area of the vertical channels is sufficiently small, the displaced air flowing into and through the vertical channels will create a sufficiently high positive pressure in the vertical channels to prevent biological fluid from entering the vertical channels. The downstream surface of the BFFM's will therefore wet from the bottom up and the displaced air that was within the BFFM's will continue to flow into the vertical channels, and into the circular outlet channel, and then into the outlets. When the downstream surface of the respective BFFM's has become wetted to the level of the top of vertical channels 22a, air flow through the two outermost vertical channels 22a will stop because the downstream surface of the BFFM's below the top of the two outermost vertical channels will be wetted. Therefore the pressure in the two outermost vertical channels will decrease allowing biological fluid to enter the two outermost vertical channels from the bottom up, thereby displacing the air that was in the two outermost vertical channels. At the same time the wetted level of the downstream surface of the BFFM's will continue to wet in the vertical direction, wetting the downstream surface of the BFFM's adjoining the respective circular outlet channel's 25. Because the cross-sectional flow area of the top of circular outlet channel's 25 is not sufficiently small to create a positive pressure in them due to the air flow through them, biological fluid will begin to flow into vertical channels 22 and into the top of circular outlet channel's 25 as BFFM's continue to wet in the vertical direction. The biological fluid flowing into vertical channels 22 and 22a, and into circular outlet channel's 25 will flow into the respective outlets 27 and 27a of BFFD 100 and then into tubing 82 toward receiving blood bag 99, and into tubing 82a toward receiving blood bag 99a. As biological fluid starts to flow into outlets 27 and 27a, the first and second BFFM's will continue to wet vertically. Hence the initial flow through circular outlet channel's 25, and through outlet 27 and 27a, will first be air, and then be a mixture of air and biological fluid, and finally biological fluid only, so that the initial flow into tubing 82 and 82a will first be air and then consist of alternate segments of biological fluid and air, and finally consist of biological fluid only. Once the BFFM's have been wetted, the flow of biological fluid through them will be uniform over their entire surface area so that the entire surface area of the BFFM's will be used to filter the biological fluid, thereby utilizing the BFFM's most efficiently. The present invention is not limited to the filter underdrain shown in FIG. 5. For example any of the filter underdrains disclosed in patent application Ser. No. 10/934,881, or in application no. PCT/US2004/029026, or in U.S. Pat. No. 6,660,171 could also be used in the present invention.

The second condition that can occur after tube clamp 95 is opened is: BFFD 100 will wet as described in the first condition above, with the initial flow rates (i.e. the flow rates before the BFFM's have been wetted) being as described in the first condition. However, once the BFFM's have been wetted with biological fluid the flow rate through the BFFM's may increase so that the combined flow rate through the first and second BFFM will exceed the flow rate of biological fluid entering chamber 13 through inlet 5. In this case biological fluid will initially fill chamber 13 from the bottom to the top, and then after the BFFM's have been wetted, the liquid level in chamber 13 will drop to a level below the top of chamber 13. Hence, once the BFFM's have been wetted the flow rate of biological fluid through the portion of the BFFM's below the top of the liquid level in chamber 13 will be much greater than the flow rate of biological fluid through the portion of the BFFM's above the top of the liquid level in chamber 13, so that the portions of the BFFM's above the liquid level will not be properly utilized. If BFFD 100 is used to remove leukocytes from blood or blood product, the leukocyte removing capability of the BFFM's may be reduced in the second condition when measured against the first condition above. Hence in the second condition the filtered blood or blood product in the receiving blood bag's may contain more leukocytes than the filtered blood or blood product in the receiving blood bag's under the first condition. The second condition can be rectified by adding flow restrictions to first outlet 27 and second outlet 27a as shown in FIG. 2. The flow restrictions should be sized so that the combined flow rate of biological fluid through the first and second BFFM's, and therefore through outlets 27 and 27a, is less than or equal to the flow rate of biological fluid entering chamber 13 through inlet 5. The flow restrictions could be located anywhere downstream of the BFFM's. For example a first flow restriction could be located in tubing 82 between outlet 27 and first receiving blood bag 99, and a second flow restriction could be located in tubing 82a between outlet 27a and second receiving blood bag 99a. Alternately all or part of tubing 82 and tubing 82a could have a smaller inside diameter than tubing 81 and tubing 81a to create the restrictions downstream of the first and second BFFM's respectively. Flow restrictions could also be used downstream of the BFFM in a single sided BFFD. A flow restriction could be added downstream of the BFFM in any of the single sided devices disclosed in patent application Ser. No. 10/934,881 or in application no. PCT/US2004/029026.

Figure 6:
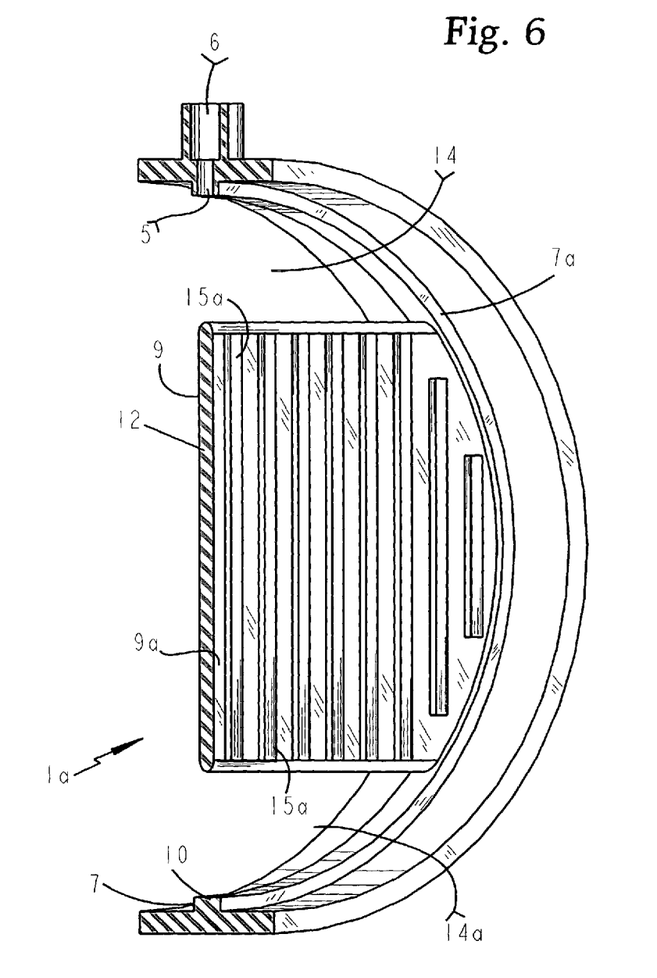
FIG. 6 is a isometric view with portions thereof removed of a housing inlet half including a baffle, that can be used to replace the housing inlet half shown in FIG. 4.

The third condition that can occur after tube clamp 95 is opens, is: If the volume of upstream chamber 13 is large enough, the BFFM's will be wetted before the liquid level in upstream chamber reaches the top of upstream chamber 13, by a combination of liquid flow through the BFFM's below the liquid level in upstream chamber 13, and capillary wetting above the liquid level, thereby allowing the air to be purged from the BFFM's. Once the BFFM's have been wetted, the air in upstream chamber 13 above the liquid level will be trapped in upstream chamber 13, because the wetted BFFM's will not allow this air to be purged from upstream chamber 13. Once the BFFM's have been wetted the flow rate of biological fluid through the portion of the BFFM's below the top of the liquid level in chamber 13 will be much greater than the flow rate of biological fluid through the portion of the BFFM's above the top of the liquid level in chamber 13, so that the portions of the BFFM's above the liquid level will not be properly utilized. If BFFD 100 is used to remove leukocytes from blood or blood product, the leukocyte removing capability of the BFFM's may be reduced in the third condition when measured against the first condition above. Hence in the third condition the filtered blood or blood product in the receiving blood bag's may contain more leukocytes than the filtered blood or blood product in the receiving blood bag's under the first condition. The third condition can be rectified by reducing the volume of upstream chamber 13. Referring to FIG. 4, the width of inner surface 10a of housing inlet half 1 (i.e. the distance between filter seal surface 7 and filter seal surface 7a) must be made sufficiently wide if the cross-sectional area of inlet 5 is to be made large enough so as not to restrict the flow of biological fluid through inlet 5. In this case the volume of upstream chamber 13 may be minimized by adding baffle 12 to inner wall 10 of housing inlet half 1a, as shown in FIG. 6. Baffle 12 extends from one side of inner wall 10 to the other side of inner wall 10. Baffle 12 may contain filter support ribs 15 located on its first surface 9, and filter support ribs 15a located on its second surface 9a as shown in FIG. 6. Housing inlet half 1a is identical to housing inlet half 1 with the exceptions that baffle 12 has been added to housing inlet half 1a, and the cross-sectional area of inlet 5a has been increased so that its cross-sectional area of inlet 5a will be greater than or equal to the cross-sectional area of the interior of tubing 81a shown in FIG. 1, and the width of inner wall 10a has been increased. However, the volume of upstream chamber 13 of housing inlet half 1a, will be less than the volume of upstream chamber 13 of housing inlet half 1, because of the volume taken up by baffle 12 and filter support ribs 15 and 15a. Baffle 12 does not act as a partition wall to divide upstream chamber 13 into two distinct and separate chambers, because of the gaps 14 and 14a above and below the top and bottom respectively, of baffle 12. The combined cross-sectional area of the two gaps should be large enough to prevent upstream chamber 13 from being divided into two separate and distinct chambers. The cross-sectional area of each gap is defined as the cross-sectional area of the gap measured in a plane that passes through the center of the baffle and that is parallel to filter seal surface 7 and filter seal surface 7a. The only purpose for adding baffle 12 to the housing inlet half is to reduce the volume of upstream chamber 13, and to add filter support ribs 15 and 15a which provide a means to keep the two BFFM's properly separated. The filter support ribs could be replaced with an array of filter support pins, or by other means. Although the baffle shown in FIG. 6 has a first gap at the top and a second gap at the bottom, a single gap at the top or bottom or anywhere in between that prevents the baffle from acting as a partition wall to divide upstream chamber 13 into two distinct and separate chambers will suffice. The gap may also be referred to as an aperture.

The fourth condition that can occur after tube clamp 95 is opens, is: If the initial combined flow rate of the first and second BFFM's exceeds the flow rate of the biological fluid entering inlet 5, the BFFM's will be wetted before the liquid level in upstream chamber reaches the top of upstream chamber 13, by a combination of liquid flow through the BFFM's below the liquid level in upstream chamber 13, and capillary wetting above the liquid level, thereby allowing the air to be purged from the BFFM's. Once the BFFM's have been wetted, the air in upstream chamber 13 above the liquid level will be trapped in upstream chamber 13, because the wetted BFFM's will not allow this air to be purged from upstream chamber 13. Once the BFFM's have been wetted the flow rate of biological fluid through the portion of the BFFM's below the top of the liquid level in chamber 13 will be much greater than the flow rate of biological fluid through the portion of the BFFM's above the top of the liquid level in chamber 13, so that the portions of the BFFM's above the liquid level will not be properly utilized. If BFFD 100 is used to remove leukocytes from blood or blood product, the leukocyte removing capability of the BFFM's may be reduced in the fourth condition when measured against the first condition above. Hence in the fourth condition the filtered blood or blood product in the receiving blood bag's may contain more leukocytes than the filtered blood or blood product in the receiving blood bag's under the first condition. The fourth condition can be rectified by reducing the initial flow rate through the BFFM's, by reducing the surface area of the BFFM's, or by increasing the resistance to flow through the BFFM's, or both.

Referring to FIG. 1 through FIG. 5, once all of the air has been purged from the first and second fluid flow paths within BFFD 100, biological fluid will continue to flow through the first fluid flow path from inlet 5 of BFFD 100 to first outlet 27 of BFFD 100, and then through tubing 82 into first receiving blood bag 99, and through the second fluid flow path from inlet 5 of BFFD 100 to second outlet 27a of BFFD 100, and then through tubing 82a into second receiving blood bag 99a until feed blood bag 98 is emptied of biological fluid. Adding flow restrictions to outlets 27 and 27a, as shown in FIG. 2, will assure that the flow of biological fluid through the first and second BFFM's will be balanced, and therefore both BFFM's will be properly utilized, and the filtered biological fluid in receiving blood bag 99 and in receiving blood bag 99a will be of the same quality. Once feed blood bag 98 has been emptied, feed blood bag 98 will be collapsed, effectively sealing the top of tubing 81, thereby preventing the flow of biological fluid in tubing 81. If first receiving blood bag 99 and second receiving blood bag 99a are positioned at a level that is sufficiently lower than BFFD 100, the pressure downstream of the first and second BFFM's will be negative. Once feed blood bag 98 collapses and biological fluid flow through the first and second fluid flow path's stop, the differential pressure across the first BFFM and second BFFM will become zero, hence the pressure in upstream chamber 13, and in the interior of tubing 81a, and in outlet 55, side port 56 and chamber 63 of DDD 50 will become negative. Because the outer surface 66 of flexible diaphragm 53 is at atmospheric pressure via inlet 57 of DDD 50, the suction force (i.e. negative pressure) will automatically drain the biological fluid from the side port 56, and from outlet 55 of DDD 50, and from tubing 81a, and from upstream chamber 13, through the BFFM's, through outlet's 27 and 27a of BFFD 100 through tubing 82 and 82a, into receiving blood bag's 99 and 99a. The suction force will automatically cause flexible diaphragm 53 to collapse so that the air that was in chamber 63 of DDD 50 will displace the biological fluid being drained from upstream of the BFFM's. As long as the volume of chamber 63 of DDD 50 is greater than or equal to the volume of biological fluid being drained, all of the biological fluid will be automatically drained as just described. If the volume of chamber 63 of DDD 50 is greater than the volume of biological fluid being drained, then flexible diaphragm 53 will only partially collapse. When the filtration cycle is complete, biological fluid will remain within the BFFM's, and in the filter under drain structure's of the first and second housing outlet half's, and in tubing 82 and 82*a*. Although DDD 50 is used as an automatic draining means in biological fluid filtration system 1000, any other automatic draining means could be used, including any of the automatic draining means disclosed in patent application Ser. No. 10/934,881 or in application no. PCT/US2004/029026.

A single sided BFFD with a single inlet and a single outlet, with a fluid flow path defined between the inlet and the outlet, with a BFFM interposed between the inlet and the outlet, and across the fluid flow path can benefit by adding a flow restriction downstream of the BFFM. If for example the single sided BFFD is used to remove leukocytes from a biological fluid, the initial flow rate of the biological fluid through the BFFM will start out high and decrease as the BFFM fouls. If the initial flow rate is too high the leukocyte removing capability of the BFFM may be reduced, so that fewer leukocytes per unit volume of filtered biological fluid will be removed from the biological fluid initially, than will be after the flow rate has been reduced due to fouling. In this case restricting the flow of biological fluid through the BFFD by using a restriction downstream of the BFFM will produce a more uniform flow rate through the BFFM throughout the entire filtration cycle, thereby increasing the leukocyte removal rate. In this case a single sided BFFD will have a single inlet and a single outlet, with a fluid flow path defined between the inlet and the outlet, with a BFFM interposed between the inlet and the outlet, and across the fluid flow path, with a flow restriction located downstream of the BFFM, with the fluid flow path flowing through the flow restriction.

A double sided BFFD that lacks a partition wall, that includes a single inlet and a single outlet, with a first fluid flow path defined between the inlet and the outlet, with a first BFFM interposed between the inlet and the outlet, and across the first fluid flow path, with a second fluid flow path defined between the inlet and the outlet, with a second BFFM interposed between the inlet and the outlet, and across the second fluid flow path, can benefit by adding a flow restriction downstream of the first and second BFFM's. If for example such a double sided BFFD is used to remove leukocytes from a biological fluid, the initial flow rate of the biological fluid through the BFFM's will start out high and decrease as the BFFM's foul. If the initial flow rate is too high the leukocyte removing capability of the BFFM's may be reduced, so that fewer leukocytes per unit volume of filtered biological fluid will be removed from the biological fluid initially, than will be after the flow rate through the BFFM's has been reduced due to fouling. In this case restricting the flow of biological fluid through the BFFD by using a restriction downstream of both the BFFM's will produce a more uniform flow rate through the BFFM's throughout the entire filtration cycle, thereby increasing the leukocyte removal rate. In this case a double sided BFFD that lacks a partition wall will have a single inlet and a single outlet, with a first fluid flow path defined between the inlet and the outlet, with a first BFFM interposed between the inlet and the outlet, and across the first fluid flow path, with a second fluid flow path defined between the inlet and the outlet, with a second BFFM interposed between the inlet and the outlet, and across the second fluid flow path, with a flow restriction located downstream of both the first and second BFFM's, with the first and second fluid flow paths flowing through the flow restriction.

A double sided BFFD, such as the ones disclosed in U.S. Pat. No. 6,660,171, and in U.S. patent application Ser. No. 10/934,881, that include a partition wall, and that include a single inlet and a single outlet, with a first fluid flow path defined between the inlet and the outlet, with a first BFFM interposed between the inlet and the outlet, and across the first fluid flow path, with a second fluid flow path defined between the inlet and the outlet, with a second BFFM interposed between the inlet and the outlet, and across the second fluid flow path, can benefit by adding a flow restriction downstream of the first and second BFFM's. If for example such a double sided BFFD is used to remove leukocytes from a biological fluid, the initial flow rate of the biological fluid through the BFFM's will start out high and decrease as the BFFM's foul. If the initial flow rate is too high the leukocyte removing capability of the BFFM's may be reduced, so that fewer leukocytes per unit volume of filtered biological fluid will be removed from the biological fluid initially, than will be after the flow rate through the BFFM's has been reduced due to fouling. In this case restricting the flow of biological fluid through the BFFD by using a restriction downstream of both the BFFM's will produce a more uniform flow rate through the BFFM's throughout the entire filtration cycle, thereby increasing the leukocyte removal rate. In this case a double sided BFFD that includes a partition wall will have a single inlet and a single outlet, with a first fluid flow path defined between the inlet and the outlet, with a first BFFM interposed between the inlet and the outlet, and across the first fluid flow path, with a second fluid flow path defined between the inlet and the outlet, with a second BFFM interposed between the inlet and the outlet, and across the second fluid flow path, with a flow restriction located downstream of both the first and second BFFM's, with the first and second fluid flow paths flowing through the flow restriction.

A double sided BFFD, such as the ones disclosed in patent application Ser. No. 10/934,881 or in application no. PCT/US2004/029026, that include a solid partition wall, and that include two inlets and two outlets, with a first fluid flow path defined between the first inlet and the first outlet, with a first BFFM interposed between the first inlet and the first outlet, and across the first fluid flow path, with a second fluid flow path defined between the second inlet and the second outlet, with a second BFFM interposed between the second inlet and the second outlet, and across the second fluid flow path, can benefit by adding a first flow restriction downstream of the first BFFM, and a second flow restriction downstream of the second BFFM. If for example such a double sided BFFC is used to remove leukocytes from a single or two independent biological fluid sources, the initial flow rate of the biological fluid or fluids through the first and second BFFM's will start out high and decrease as the BFFM's foul. If the initial flow rate is too high through either of the BFFM's, the leukocyte removing capability of the BFFM's may be reduced, so that fewer leukocytes per unit volume of filtered biological fluid or fluids through either fluid flow path will be removed from the biological fluid or fluids initially, than will be after the flow rate through the BFFM's has been reduced due to fouling. In this case restricting the flow of biological fluid or fluids through the first and second flow paths of the BFFD by using a first flow restriction downstream of the first BFFM, and a second flow restriction downstream of the second BFFM will produce a more uniform flow rate through both of the BFFM's throughout the entire filtration cycle, thereby increasing the leukocyte removal rate through both BFFM's. In this case a double sided BFFD that includes a solid partition wall will have first inlet and a first outlet, with a first fluid flow path defined between the first inlet and the first outlet, with a first BFFM interposed between the first inlet and the first outlet, and across the first fluid flow path, with a second fluid flow path defined between the second inlet and the second outlet, with a second BFFM interposed between the second inlet and the second outlet, and across the second fluid flow path, with a first flow restriction located downstream of the first BFFM, with a second flow restriction located downstream of the second BFFM with the first fluid flow path flowing through the first flow restriction, and with the second fluid flow path flowing through the second flow restriction.

Figure 7:
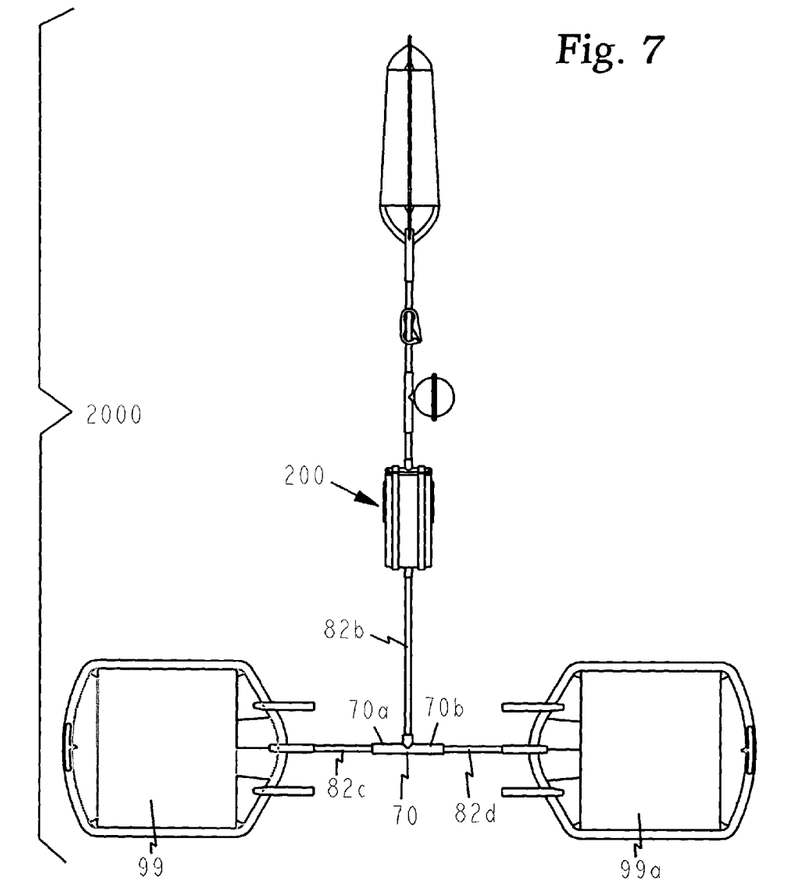
FIG. 7 is a side view of a second embodiment of a biological fluid filtration system constructed in accordance with the principles of the present invention, usable for the filtration of biological fluids, containing a feed blood bag, a first receiving blood bag, a second receiving blood bag, with a second embodiment of a BFFD interposed between the feed blood bag and the receiving blood bags, with a diaphragm draining device (DDD) that includes a built in flow restriction interposed between the feed blood bag and the BFFD.

A double sided BFFD, with or without a partition wall that includes a single inlet and a single outlet, with a first fluid flow path defined between the inlet and the outlet, with a first BFFM interposed between the inlet and the outlet, and across the first fluid flow path, with a second fluid flow path defined between the inlet and the outlet, with a second BFFM interposed between the inlet and the outlet, and across the second fluid flow path, can benefit by adding two flow restrictions downstream of the outlet as shown in FIG. 7. Referring to FIG. 7, double sided BFFD 200 may or may not contain a partition wall. The outlet of BFFD 200 is in fluid flow communication with the inlet of tee 70 via tubing 82b. Side arm 70a of tee 70 is in fluid flow communication with the inlet of receiving blood bag 99 via tubing 82c, and side arm 70b of tee 70 is in fluid flow communication with the inlet of receiving blood bag 99a via tubing 82d. A first restriction may be included in side arm 70a or in tubing 82c, while a second restriction may be included in side arm 70b or in tubing 82d. If the first and second restrictions provide equal back pressure to biological fluid flow from tubing 82b, then equal amounts of filtered biological fluid will flow into the two receiving blood bags. Furthermore as in the above cases, the two restrictions will restrict the flow of biological fluid through the BFFD, thereby producing a more uniform flow rate through the BFFM's throughout the entire filtration cycle, thereby increasing the leukocyte removal rate.

Although the filter underdrain structure shown in FIG. 5 is used in BFFD 100 shown in FIGS. 1 and 2, any other type of filter underdrain structure that provides the proper support for the BFFM can be used.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. Any combination of the various features of the described embodiments are deemed to fall within the purview of these inventive concepts.

What is claimed is:

1. A biological fluid filtration device comprising:
a housing having an inlet, a first outlet, and a second outlet, and defining a first fluid flow path between the inlet and the first outlet, and a second fluid flow path between the inlet and the second outlet, wherein the housing essentially lacks a solid partition wall between the first fluid flow path and the second fluid flow path,
a first biological fluid filtration media, having an upstream surface and a downstream surface, interposed between the inlet and the first outlet and across the first fluid flow path, wherein the first biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element,
a second biological fluid filtration media, having an upstream surface and a downstream surface, interposed between the inlet and the second outlet and across the second fluid flow path, wherein the second biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element,
an upstream chamber including a space between the first biological fluid filtration media and the second biological fluid filtration media, with the upstream surface of the first biological fluid filtration media opposing the upstream surface of the second biological fluid filtration media with all of the fluid that flows through the first fluid flow path flowing from the inlet, through the first biological fluid filtration media, and out of the first outlet, so that all of the fluid that flows through the first fluid flow path and exits the first outlet is filtered only by the first biological fluid filtration media, and
with all of the fluid that flows through the second fluid flow path flowing from the inlet, through the second biological fluid filtration media, and out of the second outlet, so that all of the fluid that flows through the second fluid flow path and exits the second outlet is filtered only by the second biological fluid filtration media,
with the amount of fluid flowing through the first fluid flow path and the second fluid flow path being essentially equal,
with the fluid flowing through the first fluid flow path being filtered simultaneously with the fluid flowing through the second fluid flow path,
so that all of the fluid that exits the first outlet can be collected in a first collection container, and so that all of the fluid that exits the second outlet can be collected in a second collection container.

2. The biological fluid filtration device of claim 1 wherein the first biological fluid filtration media and the second biological fluid filtration media are capable of removing leukocytes from a biological fluid.

3. The biological fluid filtration device of claim 1 wherein a first flow restriction is located downstream of the first biological fluid filtration media and upstream of the first outlet, and wherein a second flow restriction is located downstream of the second biological fluid filtration media and upstream of the second outlet.

4. The biological fluid filtration device of claim 1 wherein a first flow restriction is disposed within the first outlet, and wherein a second flow restriction is disposed within the second outlet.

5. The biological fluid filtration device of claim 1 wherein the housing includes a baffle disposed within said upstream chamber, and interposed between the first biological fluid filtration media and the second biological fluid filtration media, and wherein said baffle includes at least one aperture, with the cross-sectional area of said aperture being sufficiently large to prevent said upstream chamber from being divided into two distinct and separate chambers, said baffle thereby reducing the volume of said upstream chamber.

6. A method for processing a biological fluid comprising:
Passing a biological fluid into the filter device of claim 1;
Passing a portion of the biological fluid along the first fluid flow path through a first biological fluid filtration media, the first biological fluid filtration media having an upstream surface and a downstream surface, with the first biological fluid filtration media being interposed between the inlet and the first outlet and across the first fluid flow path, passing another portion of the biological fluid along the second fluid flow path through a second biological fluid filtration media, the second biological fluid filtration media having an upstream surface and a downstream surface, with the second biological fluid filtration media being interposed between the inlet and the second outlet and across the second fluid flow path thereby filtering two units of biological fluid of approximately the same volume simultaneously at approximately the same flow rate, and that will run automatically, and minimize hold up volume, and thereby the filtered biological fluid of the two units will be of the same quality.

7. The method of claim 6 wherein the first biological fluid filtration media and the second biological fluid filtration media are capable of removing leukocytes from a biological fluid.

8. The method of claim 6 wherein a first flow restriction is located downstream of the first biological fluid filtration media, and wherein a second flow restriction is located downstream of the second biological fluid filtration media.

9. The method of claim 6 wherein the housing of the biological fluid filtration device includes a baffle disposed within said upstream chamber, and interposed between the first biological fluid filtration media and the second biological fluid filtration media, and wherein said baffle includes at least one aperture, with the cross-sectional area of said aperture being sufficiently large to prevent said upstream chamber from being divided into two distinct and separate chambers, said baffle thereby reducing the volume of said upstream chamber.

10. The method of claim 9 wherein said baffle includes at least one filter support rib on its first surface, and at least one filter support rib on its second surface.

11. The biological fluid filtration device defined in claim 1, wherein the first outlet, and the second outlet are proximate the top of the biological fluid filtration device.

12. The biological fluid filtration device defined in claim 11, wherein the inlet is proximate the top of the biological fluid filtration device.

13. The biological fluid filtration device defined in claim 1, wherein said device further includes a first downstream chamber located between the downstream surface of said first biological fluid filtration media and said housing, with the first outlet being in direct fluid flow of communication with said first downstream chamber, and wherein said device further includes a second downstream chamber located between the downstream surface of said second biological fluid filtration media and said housing, with the second outlet being in direct fluid flow communication with said second downstream chamber.

14. The biological fluid filtration device defined in claim 13, wherein said first outlet is located near the top of said first downstream chamber, thereby allowing the initial air in said first downstream chamber to vent from said first downstream chamber when said first downstream chamber fills from the bottom to the top with liquid, and wherein said second outlet is located near the top of said second downstream chamber, thereby allowing the initial air and said second downstream chamber to vent from said second downstream chamber when said second downstream chamber fills from the bottom to the top with liquid.

15. The method defined in claim 6, wherein the first outlet is connected to a first receiving blood bag, and wherein the second outlet is connected to a second receiving blood bag, with a first quantity of biological fluid that passes through the first flow path being filtered only by said first biological fluid filtration media, and then being collected in said first receiving blood bag, and with a second quantity of biological fluid that passes through the second fluid flow path being filtered only by said second biological fluid filtration media, and then being collected in said second receiving blood bag, thereby allowing said first quantity and said second quantity to be filtered simultaneously.

16. A biological fluid filtration device comprising:
a housing having an inlet, a first outlet, and a second outlet, and defining a first fluid flow path between the inlet and the first outlet, and a second fluid flow path between the inlet and the second outlet, wherein the housing essentially lacks a solid partition wall between the first fluid flow path and the second fluid flow path,
a first biological fluid filtration media, having an upstream surface and a downstream surface, interposed between the inlet and the first outlet and across the first fluid flow path, wherein the first biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element,
a second biological fluid filtration media, having an upstream surface and a downstream surface, interposed between the inlet and the second outlet and across the second fluid flow path, wherein the second biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element,
an upstream chamber including a space between the first biological fluid filtration media and the second biological fluid filtration media, with the upstream surface of the first biological fluid filtration media opposing the upstream surface of the second biological fluid filtration media,
so that a first portion of biological fluid that enters the inlet will pass through the space between the biological fluid filtration media, and then be filtered only by the first biological fluid filtration media, with said first portion exiting through the first outlet, and
so that a second portion of biological fluid that enters the inlet will pass through the space between the biological fluid filtration media, and then be filtered only by the second biological fluid filtration media, with said second portion exiting through the second outlet,
with the first and second portions of biological fluid essentially being of equal volume and being filtered simultaneously, and independently of one another.

17. A method for processing a biological fluid comprising:
Passing a biological fluid into the filter device of claim 16;
Passing a portion of the biological fluid along the first fluid flow path through a first biological fluid filtration media, the first biological fluid filtration media having an upstream surface and a downstream surface, with the first biological fluid filtration media being interposed between the inlet and the first outlet and across the first fluid flow path, passing another portion of the biological fluid along the second fluid flow path through a second biological fluid filtration media, the second biological fluid filtration media having an upstream surface and a downstream surface, with the second biological fluid filtration media being interposed between the inlet and the second outlet and across the second fluid flow path, So that a first portion of biological fluid that enters the inlet will pass through the space between the biological fluid filtration media, and then be filtered only by the first biological fluid filtration media, with said first portion exiting through the first outlet, and So that a second portion of biological fluid that enters the inlet will pass through the space between the biological fluid filtration media, and then be filtered only by the second biological fluid filtration media, with said second portion exiting through the second outlet, With the first and second portions of biological fluid essentially being of equal volume and being filtered simultaneously, and independently of one another.

18. A biological fluid filtration device comprising:

a housing having an inlet, a first outlet, and a second outlet, and defining a first fluid flow path between the inlet and the first outlet, and a second fluid flow path between the inlet and the second outlet, wherein the housing essentially lacks a solid partition wall between the first fluid flow path and the second fluid flow path, a first biological fluid filtration media, having an upstream surface and a downstream surface, interposed between the inlet and the first outlet and across the first fluid flow path, wherein the first biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element, a second biological fluid filtration media, having an upstream surface and a downstream surface, interposed between the inlet and the second outlet and across the second fluid flow path, wherein the second biological fluid filtration media comprises at least a first filter element comprising at least one layer of porous filter material of a first pore size, and a second filter element comprising at least one layer of porous filter material of a second pore size smaller than the first pore size, and wherein the first filter element is upstream of the second filter element, an upstream chamber including a space between the first biological fluid filtration media and the second biological fluid filtration media, with the upstream surface of the first biological fluid filtration media opposing the upstream surface of the second biological fluid filtration media, wherein a first flow restriction is disposed within the first outlet and a second flow restriction is disposed within the second outlet, with the first and second portions of biological fluid essentially being of equal volume and being filtered simultaneously, and independently of one another, and wherein the housing of the biological fluid filtration device includes a baffle disposed within said upstream chamber, and interposed between the first biological fluid filtration media and the second biological fluid filtration media, and wherein said baffle includes at least one aperture, with the cross-sectional area of said aperture being sufficiently large to prevent said upstream chamber from being divided into two distinct and separate chamber, said baffle thereby reducing the volume of said upstream chamber.

19. A method for processing a biological fluid comprising:

i. Passing a biological fluid into the filter device of claim 18 with the biological fluid entering the inlet of the filter device, with a first portion of the biological fluid that flows into the inlet flowing through the first biological fluid filtration media, and out of the first outlet, so that all of the fluid that flows through the first fluid flow path and exits the first outlet is filtered only by the first biological fluid filtration media, and with a second portion of the biological fluid that flows into the inlet flowing through the second biological fluid filtration media, and out of the second outlet, so that all of the fluid that flows through the second outlet is filtered only by the second biological fluid filtration media, and with the first and second portions of biological fluid essentially being of equal volume and being filtered simultaneously, and independently of one another, and ii. collecting the biological fluid exiting the first and second outlets.

20. The biological fluid filtration device of claim 1 wherein a first flow restriction is located downstream of the first biological fluid filtration media and upstream of a first receiving blood bag, and wherein a second flow restriction is located downstream of the second biological fluid filtration media and upstream of a second receiving blood bag.

* * * * *